United States Patent [19]

Oishi et al.

[11] Patent Number: 5,585,487

[45] Date of Patent: Dec. 17, 1996

[54] METHOD FOR THE PREPARATION OF β-THIOLACTAM COMPOUND

[75] Inventors: Akihiro Oishi; Yoichi Taguchi; Isao Shibuya; Tohru Tsuchiya, all of Tsukuba, Japan

[73] Assignee: Japan as represented by Director General of Agency of Industrial Science and Technology, Tokyo-to, Japan

[21] Appl. No.: 613,100

[22] Filed: Mar. 8, 1996

[30] Foreign Application Priority Data

May 26, 1995 [JP] Japan .................................. 7-127783

[51] Int. Cl.⁶ .............................................. C07D 205/095
[52] U.S. Cl. ................................................. 540/203
[58] Field of Search .......................................... 540/203

[56] References Cited

PUBLICATIONS

*Chemisch Berichte*, vol. 115, p. 3340 (1982) (with *Chem. Abstr.*, vol. 98, 98:16849c).
*Chem. Abstr.*, vol. 65, 3818c (1966).

*Primary Examiner*—James H. Reamer
*Attorney, Agent, or Firm*—Wenderoth, Lind & Ponack

[57] ABSTRACT

Disclosed is a method for the preparation of a β-thiolactam compound, i.e. a 7-substituted-2-oxa-7-azabicyclo [3.2.0]-heptan-6-thione, represented by the general formula

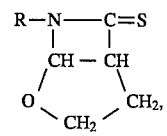

in which R is an alkyl or aryl group, having usefulness as an intermediate for the synthesis of various biologically active compounds. The compound can be prepared by the reaction of an isothiocyanate compound R—NCS, R being the same as above, and 2,3-dihydrofuran, preferably, under pressurization up to 2000 atmospheres or higher at an elevated temperature.

5 Claims, No Drawings

METHOD FOR THE PREPARATION OF β-THIOLACTAM COMPOUND

BACKGROUND OF THE INVENTION

The present invention relates to a novel method for the preparation of a β-thiolactam compound. More particularly, the present invention relates to a simple and efficient method for the preparation of a β-thiolactam compound using readily available starting materials, which compound has usefulness as an intermediate in the synthesis of certain antibiotics having a chemical structure akin to that of penicillin or as a physiologically active substance.

β-Thiolactam compound has a chemical structure akin to that of β-lactam compounds contained in the principal skeletal structure of a large number of antibiotics including penicillin as a typical example so that β-thiolactam compounds are expected, like β-lactam compounds, to play a core role in physiologically active agents.

In fact, it is known that β-thiolactam compounds having chemical structures resembling that of penicillin have antimicrobial activity according to the report appearing, for example, in Journal of the American Chemical Society, volume 97, page 5628 (1975). It is also known that some β-thiolactam compounds have a sedative or anticonvulsive activity. See, for example, South African Patent No. 6707, 088; Chem. Abstr. volume 70, 57602x (1969).

As a method for the synthetic preparation of a β-thiolactam compound, a method generally applicable involves a reaction of a β-lactam compound corresponding to the desired β-thiolactam compound with phosphorus pentasulfide, boron sulfide or Lawesson reagent, i.e. (p-methoxyphenyl)thionophosphine sulfide dimer. See, for example, Chemische Berichte, volume 118, page 653 (1985). As a method for the formation of a β-thiolactam ring, a method is disclosed in Chemische Berichte, volume 109, page 906 (1976), according to which a thioketene compound and a Schiff base are subjected to a [2+2] addition cyclization reaction.

These methods, however, do not provide a means for the direct formation of a β-thiolactam compound having a structure resulting from condensation of a furan ring. If it ever be possible to accomplish such a structure, many problems to be solved remain unsolved for industrialization including low availability of the starting materials and complexity of the process involving a number of steps.

With an object to provide a simple and efficient method for the synthetic preparation of a β-thiolactam compound capable of solving the above described problems in the prior art methods, the inventors have continued extensive investigations on β-lactam compounds having correlation with β-thiolactam compounds and previously discovered that a novel β-lactam compound can be prepared in a high yield by the reaction of 2,3-dihydrofuran and an isocyanate ester compound and that a monocyclic β-lactam compound can be obtained by the reaction of an alkyl vinyl ether and an isocyanate ester compound.

SUMMARY OF THE INVENTION

The present invention accordingly has an object to provide a simple, highly efficient and versatile method for the synthetic preparation of various kinds of β-thiolactam compounds to be freed from the above described disadvantages and limitations in the prior art methods.

Thus, the method of the present invention for the preparation of a β-thiolactam compound represented by the general formula

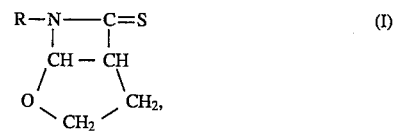

in which R is an alkyl group or an aryl group, which comprises the step of: uniformly mixing an isothiocyanate compound represented by the general formula

in which the symbol R has the same meaning as defined above, and 2,3-dihydrofuran.

It is preferable that the mixture of the isothiocyanate compound and 1,2-dihydrofuran is heated at an elevated temperature or brought under a superatmospheric pressure in order to accelerate the reaction.

Although the reaction between the isothiocyanate compound and 2,3-dihydrofuran is performed usually at an elevated temperature, the reaction can proceed even at room temperature under a high pressure of, for example, 2000 atmosphere or higher.

DETAILED DESCRIPTION OF THE PREFERRED EMBODIMENTS

As is described above, the procedure of the inventive method for the preparation of a β-thiolactam compound is very simple and efficient because the synthetic reaction can proceed only by uniformly mixing the two kinds of the starting materials to give the desired compound in a high yield.

One of the starting reactants is an isothiocyanate compound represented by the above given general formula (II). In this general formula, R is a monovalent hydrocarbon group including alkyl and aryl groups. The alkyl group is exemplified by straight-chain, branched and cyclic alkyl groups having 1 to 70 carbon atoms such as methyl, ethyl, n-propyl, isopropyl, n-butyl, isobutyl, sec-butyl, tert-butyl, pentyl, hexyl, octyl, decyl, cyclopentyl and cyclohexyl groups. Aryl-substituted alkyl groups such as benzyl and 2-phenylethyl groups are also suitable. The aryl group is exemplified by those having 6 to 10 carbon atoms such as phenyl, tolyl, xylyl, naphthyl, ethylphenyl, n-propylphenyl and isopropylphenyl groups. The aryl group can be substituted on the aromatic ring by a substituent including lower alkyl groups, lower alkoxy groups and halogen atoms as exemplified by methoxyphenyl, ethoxyphenyl, n-propoxyphenyl, isopropoxyphenyl, fluorophenyl, chlorophenyl, bromophenyl and iodophenyl groups.

Particular examples of the isothiocyanate ester compound represented by the general formula (II) and suitable as the starting reactant in the inventive method include: methyl isothiocyanate, ethyl isothiocyanate, phenyl isothiocyanate, tolyl isothiocyanate, xylyl isothiocyanate, methoxyphenyl isothiocyanate, chlorophenyl isothiocyanate and benzyl isothiocyanate.

The reaction of the isothiocyanate ester compound of the general formula (II) and 2,3-dihydrofuran proceeds in a molar ratio of 1:1 of these reactants but it is usually preferable that 2,3-dihydrofuran is used in a large excess over the isothiocyanate compound so that the excess amount of 2,3-dihydrofuran serves as a diluent of the reaction mixture although it is optional that 2,3-dihydrofuran is used in an amount of about 2 moles per mole of the isothiocyanate compound and the reaction mixture is diluted with a conventional inert organic solvent, which should preferably have relatively low polarity, such as aliphatic, alicyclic and aromatic hydrocarbon solvents. Preferable solvents include, for example, hexane, heptane, octane, decane, cyclohexane, cyclodecane, tetrahydronaphthalene, decahydronaphthalene, benzene, toluene, xylene, ethylbenzene and the like.

The reaction between the isothiocyanate compound and 2,3-dihydrofuran proceeds, though not essential, by bringing the reaction mixture under a superatmospheric pressure which should preferably be as high as possible even at such a temperature at which the reaction does not proceed under normal pressure. The pressure should desirably be at least 2000 atmospheres or, preferably, in the range from 2000 to 10000 atmospheres. The reaction temperature is not particularly limitative and the reaction can proceed even at room temperature although the reaction can be accelerated by increasing the temperature while an excessively high temperature is disadvantageous due to increase in the side reactions. In consideration of the balance between the reaction velocity and side reactions, the reaction temperature should be in the range from 0° to 200° C. or, preferably, from 20° to 150° C. The reaction time naturally depends on various factors such as the kinds of the isothiocyanate compound and solvent, pressure, reaction temperature and the like but the reaction is usually complete within 1 to 50 hours. In this way, the desired β-thiolactam compound can be obtained in a high yield of, for example, 50% or even higher of the theoretical value though dependent on various conditions.

In the following, the method of the present invention is described in more detail by way of examples.

EXAMPLE 1

A mixture consisting of 0.68 g (5.0 mmoles) of phenyl isothiocyanate and 1.76 g (25 mmoles) of 2,3-dihydrofuran was sealed in a Teflon tube and heated in an autoclave at 130° C. for 20 hours under a pressure of 10 atmospheres to effect the reaction between the reactants. After completion of the reaction time, the reaction mixture taken out of the autoclave and freed from unreacted 2,3-dihydrofuran by distillation under reduced pressure was subjected to column chromatography through a silica gel column using a 1:1 by volume mixture of hexane and ethyl acetate as the developer to obtain 0.54 g of a purified product having a melting point of 59° C. which could be identified from the identification data shown below to be 7-phenyl-2-oxa-7-azabicyclo[3.2.0] heptan-6-thione which is a compound of the general formula (I) with R being a phenyl group. The above mentioned yield of this product compound corresponds to 52% of the theoretical value.

Infrared absorption spectrum: 1499 cm$^{-1}$ (N—C=S)

Mass spectrometry (m/z): 205 (M$^+$) (C$_{11}$H$_{11}$NOS=205)

$^1$H—NMR: (δ, ppm) 8.02–7.98 (m, 2H), 7.40–7.34 (m, 2H), 7.25–7.19 (m, 1H), 6.2 (d, J=3 Hz, 1H), 4.27 (t, J=9 Hz, 1H), 3.95–3.86 (m, 1H) , 3.72 (dd, J=3, 7 Hz, 1H) , 2.28 (dd, J=5, 13 Hz, 1H), 1.97–1.83 (m, 1H)

$^{13}$C—NMR: (δ, ppm) 198.73, 137.74, 128.97, 2C, 126.17, 117.56, 2C, 92.05, 67.52, 58.04, 27.11

Elementary analysis: (%)

|  | C | H | N | S |
|---|---|---|---|---|
| calculated for C$_{11}$H$_{11}$NOS | 64.36 | 5.40 | 6.83 | 15.62 |
| found | 64.37 | 5.39 | 6.85 | 15.16 |

EXAMPLE 2

The experimental procedure was substantially the same as in Example 1 excepting replacement of 0.68 g of the phenyl isothiocyanate with 0.41 g (5.6 mmoles) of methyl isothiocyanate to give 0.14 g of a reaction product which could be identified to be 7-methyl-2-oxa-7-azabicyclo[3.2.0]heptan-6-thione which is a compound of the general formula (I) with R being a methyl group. The yield of the product was 17% of the theoretical value.

Infrared absorption spectrum: 1508 cm$^{-1}$ (N—C=S)

Mass spectrometry (m/z): 143 (M$^+$) (C$_6$H$_9$NOS=143)

$^{13}$C—NMR: (δ, ppm) 203.59, 93.24, 67.45, 58.58, 29.06, 26.46

EXAMPLE 3

The experimental procedure was substantially the same as in Example 1 excepting replacement of 0.68 g of the phenyl isocyanate with 0.85 g (5.0 mmoles) of 4-chlorophenyl isothiocyanate to give 0.47 g of a reaction product which could be identified to be 7-(4-chlorophenyl)-2-oxa-7-azabicyclo[3.2.0]-heptan-6-thione which is a compound of the general formula (I) with R being a 4-chlorophenyl group. The yield of the product was 39% of the theoretical value.

Infrared absorption spectrum: 1495 cm$^{-1}$ (N—C=S)

$^{13}$C—NMR: (δ, ppm) 198.92, 136.30, 131.18, 129.14, 2C, 118.92, 2C, 92.27, 67.69, 58.38, 27.22

EXAMPLE 4

The experimental procedure was substantially the same as in Example 1 excepting replacement of 0.68 g of the phenyl isothiocyanate with 0.75 g (5.0 mmoles) of p-tolyl isothiocyanate to give 0.19 g of a reaction product which could be identified to be 7-(4-methylphenyl)-2-oxa-7azabicyclo[3.2.0]-heptan-6-thione which is a compound of the general formula (I) with R being a p-tolyl group. The yield of the product was 17% of the theoretical value.

infrared absorption spectrum: 1512 cm$^{-1}$ (N—C=S)

$^{13}$C—NMR: (δ, ppm) 198.08, 135.43, 129.49, 2C, 117.67, 2C, 114.81, 92.10, 67.54, 57.99, 27.13, 21.18

EXAMPLE 5

The experimental procedure was substantially the same as in Example 1 excepting replacement of 0.68 g of the phenyl isothiocyanate with 0.85 g (5.1 mmoles) of 4-methoxyphenyl isothiocyanate to give 0.33 g of a reaction product which could be identified to be 7-(4-methoxyphenyl)-2-oxa-7-azabicyclo[3.2.0]- heptan-6-thione which is a compound of the general formula (I) with R being a 4-methoxyphenyl group. The yield of the product was 27% of the theoretical value.

Infrared absorption spectrum: 1572 cm$^{-1}$ (N—C=S)

$^{13}$C—NMR: (δ, ppm) 197.18, 757.62, 137.36, 779.33, 2C, 114.10, 2C, 92.25, 67.57, 57.95, 55.49, 27.05

EXAMPLE 6

A mixture consisting of 0.68 g (5.0 mmoles) of phenyl isothiocyanate and 7.76 g (25 mmoles) of 2,3-dihydrofuran was sealed in a Teflon tube which was heated in a high-pressure reactor at 100° C. for 20 hours under a pressure of 2000 atmospheres to effect the reaction. After the above mentioned reaction time, the reaction mixture was taken out of the reactor and subjected to a quantitative analysis by the GLC method with hexadecane as an internal standard to find that the desired product, i.e. 7-phenyl-2-oxa-7-azabicyclo [3.2.0]-heptan-6-thione, was formed in a yield of 55% based on the theoretical value.

To examine the effect of the pressure on the reaction, the same synthetic procedure as above was repeated except that the pressure was decreased to 6 atmospheres to find that the yield of the desired product was only 17% of the theoretical value.

EXAMPLE 7

A mixture consisting of 1.37 g (10 mmoles) of phenyl isothiocyanate and 3.51 g (50 mmoles) of 2,3-dihydrofuran was sealed in a Teflon tube which was heated in a high-pressure reactor at 40° C. for 20 hours under a pressure of 8000 atmospheres to effect the reaction. After the above mentioned reaction time, the reaction mixture was taken out of the reactor and analyzed in the same manner as in Example 6 to find that the yield of the desired product, i.e. 7-phenyl-2-oxa-7-azabicyclo[3.2.0]heptan-6-thione, was 29% of the theoretical value.

To examine the effect of the pressure on the reaction, the same synthetic procedure as above was repeated except that the Teflon tube containing the reaction mixture was heated at 40° C. for 20 hours under normal pressure. The results of the reaction was that the desired product could not be obtained at all.

EXAMPLE 8

A mixture consisting of 0.68 g (5.0 mmoles) of phenyl isothiocyanate, 0.71 g (10 mmoles) of 2,3-dihydrofuran and 1.5 ml of toluene was sealed in a Teflon tube which was heated in a high-pressure reactor at 100° C. for 20 hours under a pressure of 4000 atmospheres to effect the reaction. After the above mentioned reaction time, the reaction mixture was taken out of the reactor and analyzed in the same manner as in Example 6 to find that the yield of the desired product, i.e. 7-phenyl-2-oxa-7-azabicyclo-[3.2.0]heptan-6-thione, was 48% of the theoretical value.

To examine the effect of the presence of toluene on the reaction, the same synthetic procedure as above was repeated excepting omission of toluene in the reaction mixture to find that the yield of the desired product was only 8% of the theoretical value.

What is claimed is:

1. A method for the preparation of a β-thiolactam compound which is a 7-substituted-2-oxa-7-azabicyclo[3.2.0] heptan-6-thione represented by the general formula

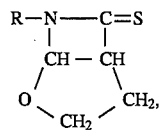

in which R is an alkyl group or an aryl group, which comprises the step of:
uniformly mixing an isothiocyanate compound represented by the general formula

R—NCS, in which the symbol R has the same meaning as defined above, and 2,3-dihydrofuran to form a mixture.

2. The method for the preparation of a β-thiolactam compound as claimed in claim 1 in which the mixture of the isothiocyanate compound and 2,3-dihydrofuran is brought under a pressure of 2000 atmospheres or higher.

3. The method for the preparation of a β-thiolactam compound as claimed in claim 1 in which the mixture of the isothiocyanate compound and 2,3-dihydrofuran is kept at a temperature in the range from 0° to 200° C.

4. The method for the preparation of a β-thiolactam compound as claimed in claim 1 in which the amount of 2,3-dihydrofuran is at least 2 moles per mole of the isothiocyanate compound.

5. The method for the preparation of a β-thiolactam compound as claimed in claim 1 in which the mixture of the isothiocyanate compound and 2,3-dihydrofuran is diluted with an organic solvent selected from the group consisting of aliphatic hydrocarbon solvents, alicyclic hydrocarbon solvents and aromatic hydrocarbon solvents.

\* \* \* \* \*